(12) United States Patent
Gwen

(10) Patent No.: US 6,752,158 B1
(45) Date of Patent: Jun. 22, 2004

(54) FLOSSER APPARATUS WITH LOCKABLE FLOSS TIGHTENER

(76) Inventor: Patrick Gwen, 3443 Leeland, Houston, TX (US) 77003

( * ) Notice: Subject to any disclaimer, the term of this patent is extended or adjusted under 35 U.S.C. 154(b) by 0 days.

(21) Appl. No.: 10/212,407

(22) Filed: Aug. 6, 2002

Related U.S. Application Data

(63) Continuation-in-part of application No. 10/172,054, filed on Jun. 17, 2002.

(51) Int. Cl.[7] .............................................. A61C 15/00
(52) U.S. Cl. ...................................................... 132/327
(58) Field of Search ................................. 132/323–328

(56) References Cited

U.S. PATENT DOCUMENTS

| | | | |
|---|---|---|---|
| 2,187,899 A | | 1/1940 | Henny |
| 2,648,341 A | | 8/1953 | Moll |
| 3,631,869 A | * | 1/1972 | Espinosa .................... 132/323 |
| 3,783,883 A | * | 1/1974 | Alexander ................... 132/323 |
| D251,074 S | * | 2/1979 | Schiff ........................... D28/68 |
| D251,075 S | * | 2/1979 | Schiff ........................... D28/68 |
| 4,192,330 A | * | 3/1980 | Johnson ....................... 132/323 |
| 4,280,518 A | | 7/1981 | Gambaro |
| D276,088 S | | 10/1984 | Fong |
| 4,522,216 A | | 6/1985 | Bunker |
| 5,016,660 A | | 5/1991 | Boggs |
| 5,538,023 A | | 7/1996 | Oczkowski et al. |
| 5,692,531 A | | 12/1997 | Chodorow |
| 5,829,458 A | | 11/1998 | Chodorow |
| 6,065,479 A | * | 5/2000 | Chodorow ................... 132/323 |

FOREIGN PATENT DOCUMENTS

| | | |
|---|---|---|
| DE | 29 23 057 | 12/1980 |
| DE | 38 31 039 | 3/1990 |

\* cited by examiner

*Primary Examiner*—Kevin Shaver
*Assistant Examiner*—Stephanie L Willatt
(74) *Attorney, Agent, or Firm*—Harrison & Egbert

(57) ABSTRACT

A flosser apparatus having a body with a first fork member and a second fork member, a flexible member interposed between the fork members, and a length of floss having one end affixed to the first fork member and an opposite end affixed to the second fork member. The flexible member is cooperative with the fork members such that the fork members move away from each other upon an application of a force onto the flexible member in a direction transverse to the direction of the length of floss. A surface on the flexible member is engageable with a surface of the body so as to fix the floss in a tightened condition.

17 Claims, 2 Drawing Sheets

FLOSSER APPARATUS WITH LOCKABLE FLOSS TIGHTENER

RELATED U.S. APPLICATIONS

The present application is a continuation-in-part of U.S. application Ser. No. 10/172,054 filed on Jun. 17, 2002 and entitled "Flosser Apparatus with Floss Tightening Mechanism", presently pending.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to appliances for using floss on human teeth. More particularly, the present invention relates to flossers that contain a strand of floss. Additionally, the present invention relates to flosser apparatus which have the ability to tighten the floss.

BACKGROUND OF THE INVENTION

It has been well known in the past to provide some form of an implement to facilitate the removing of food particles from between a person's teeth. Such items have been frequently referred to as a toothpick and generally take the form of an elongated pointed tool which is adapted to be inserted between a person's teeth and moved in order to dislodge any food particles and plaque located between the teeth.

It has been further found to be desirable to not only employ the use of a pointed instrument, but also to employ the use or a strand of thread which is commonly referred to as dental floss. A segment from the dental floss is to be stretched taut and then inserted between the person's teeth and moved back and forth in order to effect removal of any lodged food particles and plaque.

Over time, various persons have discovered that it is practical and useful to apply a segment of a strand of dental floss into an implement that can be inserted into the mouth and manipulated so as to properly control the application of the floss. These devices are commonly known as "flossers". These devices provide a convenient mechanism for the flossing of teeth without the need for lengthy strands of floss. They also serve to more effectively reach into the spaces between the teeth so as to carry out flossing activities in a more effective manner.

In the past, various patents have issued relating to such flosser implements.

The earliest flosser apparatus that was revealed is in U.S. Pat. No. 2,187,899, issued on Jan. 23, 1940 to I. Henny. This patent describes a dental floss throw-away unit in which a single strand of thread extends between outwardly extending arms. A head is formed with the arms extending radially outwardly therefrom. The strand of floss extends in parallel relationship to the back of the head.

U.S. Pat. No. 2,648,341, issued on Aug. 11, 1953 to S. Moll teaches a dental floss holder which includes an elongated flexible member formed of plastic material. One end of the flexible member is rounded and provided with a transverse bore. A length of dental floss will extend through the transverse bore.

German Patent No. 29 23 057 teaches a dental floss applicator which includes a plurality of strands of floss which are far apart and extend in a plane which is perpendicular to the holder portion. Since the strands are not aligned with the shank portion of this flosser device, they are relatively difficult to apply as floss to one's teeth. The flosser is removably secured within a U-shaped head portion.

U.S. Pat. No. 4,280,518, issued on Jul. 28, 1981 to S. M. Gambaro teaches a tooth cleaning implement which includes an elongated member which has, at one end. a strand of dental floss tautly stretched thereacross. The opposite end of the elongated member is attached to a brush-like member which is used to facilitate the cleaning of teeth and dental bridges.

U.S. Design Pat. No. 276,088, issued on Oct. 23, 1984 to A. Fong describes a conventional flosser apparatus in which a single strand of floss is retained between a pair of arms extending outwardly of a head portion. A strand is connected to the head portion and extends so as to terminate at a pointed end.

U.S. Pat. No. 4,522,216, issued on Jun. 11, 1985, to R. L. Bunker describes a dental floss applicator which comprises a solid rectangular shaped body fitted with a pair of adjacent end arms forming a yolk arrangement in which the floss is drawn so as to form an X-shaped pattern. A small button fastener on each side of the applicator body permits the fastening of the floss after it has been stretched taut around the yolk.

German Patent No. 3,831,039 issued to H. Bauer describes a device for cleaning the narrow space between a bridge and the jaw. A pair of threads are connected to a guide. The threads are arranged in parallel to each other and are connected to each other by a number of parallel transverse threads.

U.S. Pat. No. 5,016,660, issued on May 21, 1991 to M. S. Boggs describes an automatic flossing tool having reciprocating tines supporting the flossing material and biased apart so as to assure proper tension on the flossing material. The device includes a means carried out by the tines for moving the flossing material between the tines and having a removable head so as to permit replacement of the head to provide sterile use for subsequent users.

In the recent past, it has been recognized that the above-identified flosser designs are often faulty because of the difficulty in placing the floss between the teeth and the difficulty associated with removing the floss from the teeth. In other circumstances, the close spacing of teeth will make it difficult to place the floss, in a slackened condition, between the teeth. Since the floss between the arms of the flosser apparatus of these prior designs is not in a very "tensioned" condition, then the floss can become frayed when placed in between and pulled out of the teeth. In order to overcome this problem, various U.S. patents have recently issued relating to the flosser apparatus with the ability to "tension" the strand prior to application and removal from the teeth. U.S. Pat. No. 5,538,023, issued on Jul. 23, 1996 to Oczkowski et al., describes a tensioning dental flosser having a holder, a bow and a length of dental floss spanning the bow. A movable element is provided which can cause a portion of the floss holder to move and tighten the strand of floss so as to reduce the slack in the floss. U.S. Pat. No. 5,692,531, issued on Dec. 2, 1997 to I. S. Chodorow, describes a dual strand dental flosser having a body part, first and second spaced apart arms extending from the body part, a first strand of dental floss extending axially between the arms and a second strand of dental floss extending axially between the arms and generally parallel to the first strand of dental floss. A lever mechanism extends from one of the arms which is movable so as to be moved toward the body part. When this lever is moved toward the body part, the first and second strands will tighten. U.S. Pat. No. 5,829,458, issued on Nov. 3, 1998 to I. S. Chodorow, describes a dental floss holder of similar construction to that of U.S. Pat. No. 5,692,531. It shows a variety of other mechanisms that can be used for tightening the dental floss.

There is a product on the market identified as the "GLIDE (™)" floss pick and manufactured by W. L. Gore and Associates, Inc. This is another type of flosser that includes a tensioning structure. In this device, the handles of the flosser can be squeezed together so as to cause the floss-holding arms to move away from each other about a pivot point spaced from the floss and between the floss and the pivot point.

Unfortunately, in all of these prior art devices, the technique for tensioning the floss will require the application of pressure generally in the direction of the floss. However, when the floss is applied to the teeth, a force must be applied transverse to the floss so as to cause the floss to enter the spaces between the teeth. In each of these prior art devices, by applying forces in the direction of the floss, there is a difficulty in manipulating the head of the flosser so that the floss will enter the spaces between the teeth. Often, the tension-providing surfaces will be somewhat wet so as to create a sliding motion of the fingers placed thereon. It is very difficult to manipulate the flosser so that the tensioned floss is manipulated in the desired manner. Also, subsequent to use, it is difficult to tension the floss and then carry out a lifting motion whereby the floss can be removed from the teeth.

It is an object of the present invention to provide a flosser apparatus which facilitates the tensioning of the floss at the end of the flosser.

It is another object of the present invention to provide a flosser apparatus which causes the tension-providing force to be applied in a direction transverse to the direction of the floss.

It is another object of the present invention to provide a flosser apparatus whereby the floss can be more easily manipulated during the flossing of teeth.

It is a further object of the present invention to provide a flosser apparatus which avoids the shredding of the floss during use.

It is still another object of the present invention to provide a flosser apparatus which is easy to use, relatively inexpensive and easy to manufacture.

These and other objects and advantages of the present invention will become apparent from a reading of the attached specification and appended claims.

BRIEF SUMMARY OF THE INVENTION

The present invention is a flosser apparatus having a body with a first fork member and a second fork member at an end thereof, a flexible member interposed between the fork members, and a length of floss having one end affixed to the first fork member and an opposite end affixed to the second fork member. The length of floss extends in a direction. The flexible member is cooperative with the fork members such that the first and second fork members move away from each other upon the application of a force onto the flexible member in a direction transverse to the direction of the length of the floss.

In the present invention, the body has a pivot point between the first and second fork members on a side of the flexible member opposite the length of floss.

In the preferred embodiment of the present invention, the body has a first surface extending into the space and the flexible member has a second surface extending toward the first surface of the body. The first and second surfaces are engageable with each other so as to fix a position of the first fork member with respect to the second fork member. The first surface has a plurality of toothed elements extending upwardly therefrom. The second surface has a plurality of toothed elements extending downwardly therefrom. The flexible member is an arcuate member having one end affixed to the first fork member and an opposite end affixed to the second fork member. Each of the first and second fork members has a bent shape such that the length of floss is offset from the plane of the body.

In an alternative embodiment of the present invention, one of the first and second surfaces has a button element extending therefrom. The other of the first and second surfaces has an orifice formed thereon. The button element is engageable with the orifice. In particular, the button element has an arrowhead shape such that the button element is non-releasably retained within the orifice of the first surface.

In still another alternative embodiment of the present invention, the flexible member is an arcuate member movable between a concave position facing the length of floss and a convex position having a concavity facing away from the length of floss. At least one of the first and second fork members has a stop element extending inwardly to the other of the fork members. This stop element limits a movement of the flexible member toward the concave position.

DETAILED DESCRIPTION OF THE INVENTION

Figure 1:
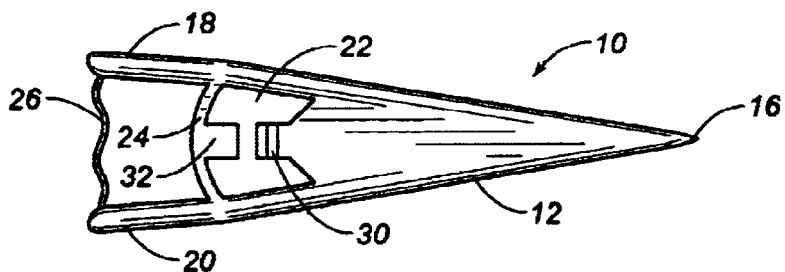
FIG. 1 is a plan view of the preferred embodiment of the present invention showing the flosser apparatus in its untensioned position.

Referring to FIG. 1, there is shown the flosser apparatus 10 in accordance with the preferred embodiment of the present invention. The flosser apparatus 10 includes a body 12 having a fork end 14 and a pointed end 16. The fork end 14 includes a first fork member 18 and a second fork member 20. A space 22 is defined between the fork members 18 and 20. A flexible member 24 is interposed between the first fork member 18 and the second fork member 20 in the space 22. A length of floss 26, shown in an untensioned position, has one end affixed to the first fork member 18 and an opposite end affixed to the second fork member 20. The length of floss 26 extends in a particular direction. In the present invention, the flexible member 24 is cooperative with the first fork member 18 and the second fork member 20 such that the fork members 18 and 20 move away from each other upon an application of force onto the flexible member 24 in a direction transverse to that of the direction of the length of floss 26.

In FIG. 1, it can be seen that the body 12 has a pivot point 28 positioned on a side of the flexible member 24 opposite the length of floss 26. The fork members 18 and 20 will pivot with respect to the pivot point 28 on the body 12. The opposite end 16 has a pointed configuration. The body 12 has a generally chevron configuration. The pointed end 16 serves as a pick, in the nature of a toothpick. The body 12 is formed of a polymeric material through an injection molding process. The floss 26 can be a single strand of floss or multiple floss strands arranged in parallel. The floss 26 can be of various materials similar to those used in existing flossers.

Importantly, in FIG. 1, it can be seen that the body 12 has a surface 30 extending in the space 22 adjacent to the pivot point 28. Similarly, the flexible member 24 has a surface 32 extending toward the surface 30. In FIG. 1, it can be seen that the first surface 30 is spaced from the second surface 32 and that the flexible member 24 has an arcuate configuration. In this arrangement, there is no pressure being applied to the inner walls of the fork members 18 and 20. As such, the floss 26 will have a generally relaxed untensioned configuration.

Figure 2:
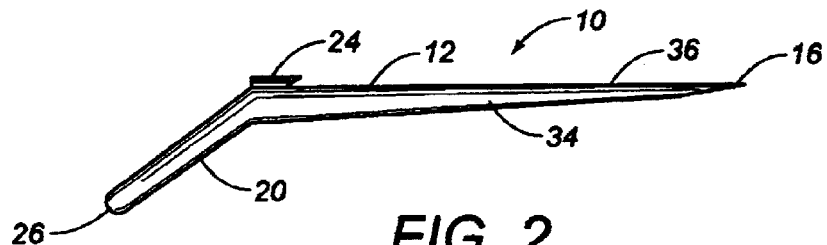
FIG. 2 is a side elevational view of the preferred embodiment of the present invention.

In FIG. 2, it can be seen that the body 12 of the flosser apparatus 10 has a generally planar portion 34 extending from the end 16 to the end of the flexible member 24. It can be seen that the flexible member 24 has a surface which extends slightly above the top surface 36 of the body 12. The fork members 18 and 20 are bent downwardly so that the floss will extend in an offset plane from that of the body 12. Relative to the illustration of FIG. 1, when it is desired to press against the surface of the arcuate flexible member 24, the finger touching the arcuate member 24 will be offset from the plane of the floss 26 at the end of the bent fork member 20.

Figure 3:
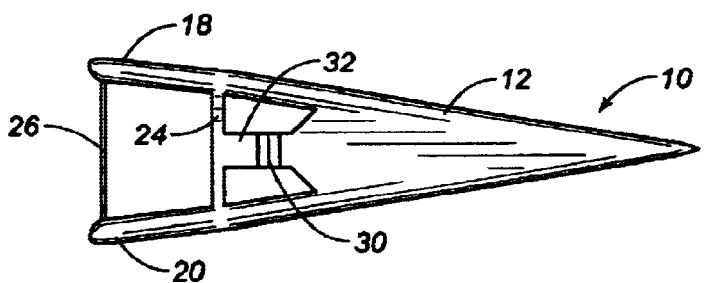
FIG. 3 is a plan view of the present invention showing the present invention in its locked tensioned position.

FIG. 3 shows a flosser apparatus 10 of the present invention with the length of floss 26 in its tensioned configuration. In particular, it can be seen that a force has been applied onto the curved surface of the arcuate member 24 so as to push the arcuate member 24 into a generally linear orientation, such as shown in FIG. 3. In this orientation, the first surface 30 will engage the second surface 32 so as to lock the flexible member 24 in this position. The force applied to the flexible member 24 is in a direction transverse to the direction of the length of floss 26. The surfaces 30 and 32 will engage each other so as to lock the flexible member 24 into a fixed position. In this orientation, the floss 26 will be suitably tensioned since the fork members 18 and 20 will be pushed away from each other by the straightening action applied to the flexible member 24.

Figure 4:
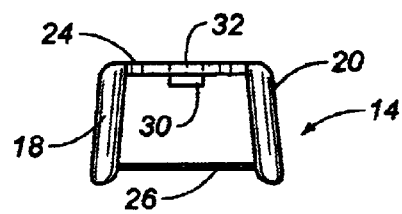
FIG. 4 is an end view showing the present invention in its tensioned position.

FIG. 4 shows an end view of the end 14 as having fork members 18 and 20 supporting the length of floss 26 therebetween. The flexible member 24 is illustrated as having its edge affixed, respectively, to the fork members 18 and 20. The surfaces 32 and 30 engage each other so as to lock the flexible member 24 into a generally linear orientation and so as to push the fork members 18 and 20 away from each other such that the length of floss 26 is suitably tensioned.

Figure 5:
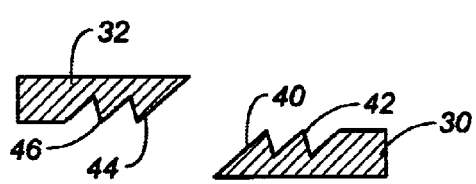
FIG. 5 is an isolated diagrammatic illustration of the locking elements associated with the flosser of the preferred embodiment of the present invention.

FIG. 5 is a detailed illustration of the surfaces 30 and 32. Surface 30 is suitably formed with the body 12 so as to have a plurality of toothed elements 40 and 42 extending upwardly therefrom. Similarly, the second surface 32 has a plurality of toothed elements 44 and 46 extending downwardly therefrom. In normal use, when the second surface 32 is brought into proximity to the first surface 30, the toothed elements 40, 42, 44 and 46 will suitably engage each other in a ratchet-like manner. In other words, the toothed element 44 will lock into a space between the toothed elements 40 and 42 so as to prevent release therefrom. As a result, the surfaces 30 and 32 will lock together until released by a lifting force applied to the respective ends of the surfaces 30 and 32.

Figure 6:
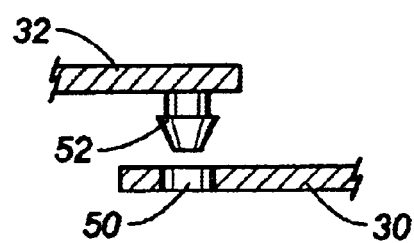
FIG. 6 is a diagrammatic illustration of a first alternative embodiment of the present invention.

FIG. 6 shows an alternative embodiment of the present invention. In FIG. 6, it can be seen that the first surface 30 has an orifice 50 formed thereon. Similarly, the second surface 32 will have a button element 52 extending downwardly therefrom. The button element 52 has a generally arrowhead-shaped configuration. When pressed through the orifice 50, the ends of the tapered configuration of the button element 52 will lock onto the inner side of surface 30 so as to lock surface 32 in a desired position upon the upper surface of surface 30. FIG. 6 simply shows an alternative technique for the locking of the flexible element 24 into its linear configuration in a manner other than the ratchet-like configuration of FIG. 5 of the preferred embodiment of the present invention.

Figure 7:
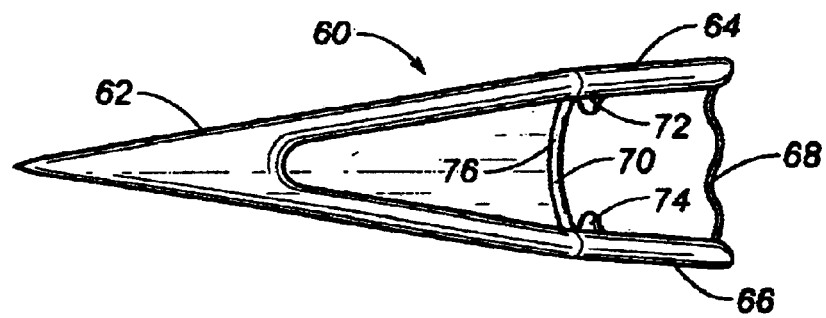
FIG. 7 is a plan view showing a second alternative embodiment of the present invention in an untensioned position.

FIG. 7 shows a second alternative embodiment of the flosser apparatus 60 in accordance with the teachings of the present invention. Flosser apparatus 60 includes a body 62 having a first fork member 64 and a second fork member 66 extending therefrom. A length of floss 68 will extend between the fork members 64 and 66 in a slackened condition. The arcuate flexible member 70 has one end affixed to the first fork member 64 and an opposite end connected 10 the second fork member 66. A first stop member 72 extends inwardly from the inner wall of fork member 64. A second stop member 74 will extend inwardly from the inner wall of fork member 66. In FIG. 7, it can be seen that the arcuate flexible member 70 has a concave surface facing the slackened floss 68.

Figure 8:
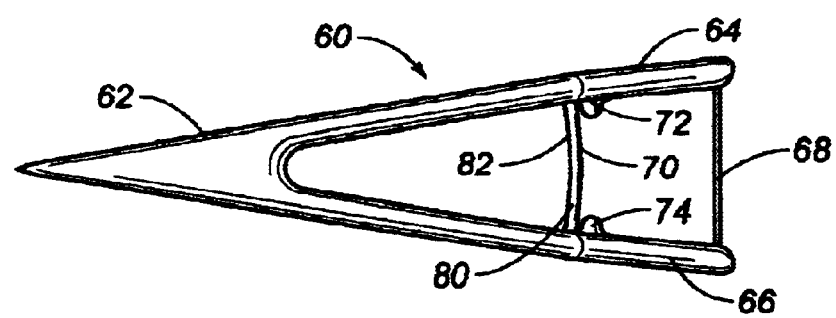
FIG. 8 is a plan view of the second alternative embodiment of the present invention showing the flosser apparatus in a tensioned position.

When it is desired to place the slackened floss 68 into a tightened condition, it is only necessary to apply a force to the surface 76 of the arcuate flexible member 70 in a direction transverse to and toward the floss 68. FIG. 8 shows the flosser apparatus 60 with the floss 68 in its tensioned condition. As can be seen, the flexible member 70 has been pushed inwardly so as to have a concave surface 80 adjacent to the floss 68 and a concave surface 82 facing away from the floss 68. Stop members 72 and 74 prevent the further inward movement of the flexible member 70 so as to "lock" the floss 68 in its tightened condition. The flexible member 70 will have sufficient flexibility so that when the force is applied to the flexible member 70, it will "flip" into the position shown in FIG. 8. A pressure applied to the convex surface 80 of the flexible member 70 will return the floss 68 to its slackened position.

The application of forces upon the flexible member 24 facilitates the insertion of the length of floss 26 between the teeth. In all circumstances, this transverse application of force, relative to the floss 26, facilitates the proper manipulation of the flosser apparatus of the present invention during flossing activities. Since the flexible member 24 locks the fork members 18 and 20 in a spaced-apart position, these fork members 18 and 20 can be strongly grasped during the flossing activities so as to facilitate the application and removal of the floss from the teeth. If less tension is desired in the floss 26, then the ratchet-like relationship between the toothed elements of the surfaces 30 and 32 can be moved from each other so as to "slacken" the floss 26. The positioning of the flexible element 24 in offset relationship to the plane of floss 26 allows the application of finger pressure onto the outer surface of the flexible member 24 without contaminating the floss 26.

The integral structure of the present invention can be quite easy to manufacture in simple molding procedures. Simpler molds can be utilized than those required for the manufacture of other, more complex flosser arrangements.

The foregoing disclosure and description of the invention is illustrative and explanatory thereof. Various charges in the details of the illustrated construction can be made within the scope of the appended claims without departing from the true spirit of the invention. The present invention should only be limited by the following claims and their legal equivalents.

I claim:

1. A flosser apparatus comprising:

a body having a first fork member and a second fork member at an end thereof, said first and second fork members having a space therebetween;

a flexible member interposed between said first and second fork members in said space; and a length of floss having one end affixed to said first fork member and an opposite end affixed to said second fork member, said length of floss extending in a direction, said flexible member being cooperative with said first and second fork members such that said first and second fork members move away from each other upon an application of a force onto said flexible member in a direction transverse to said direction of said length of floss, said body having a first surface extending into said space, said flexible member having a second surface extending toward said first surface, said first and second surfaces engaging each other so as to fix a position of said first fork member with respect to said second fork member.

2. The apparatus of claim 1, said body having a pivot point between said first and second fork members on a side of said flexible member opposite said length of floss.

3. The apparatus of claim 1, said first surface having a plurality of toothed elements extending upwardly therefrom, said second surface having a plurality of toothed elements extending downwardly therefrom.

4. The apparatus of claim 1, said flexible member comprising an arcuate member having one end affixed to said first fork member and an opposite end affixed to said second fork member.

5. The apparatus of claim 1, each of said first and second fork members having a bent shape such that said length of floss is offset from a plane of said body.

6. The apparatus of claim 1, one of said first and second surfaces having a button element extending therefrom, the other of said first and second surfaces having an orifice formed therein, said button element being engageable with said orifice.

7. The apparatus of claim 6, said button element extending downwardly from second surface, said button element having an arrowhead shape such that said button element is non-releasably retained in said orifice of said first surface.

8. A flosser apparatus comprising:

a body having a first fork member and a second fork member at an end thereof, said first and second fork members having a space therebetween;

a flexible member interposed between said first and second fork members in said space; and a length of floss having one end affixed to said first fork member and an opposite end affixed to said second fork member, said length of floss extending in a direction, said flexible member being cooperative with said first and second fork members such that said first and second fork members move away from each other upon an application of a force onto said flexible member in a direction transverse to said direction of said length of floss, said flexible member being an arcuate member moveable between a concave position facing said length of floss and a convex position having a concavity facing away from said length of floss.

9. The apparatus of claim 8, at least one of said first fork member and second fork member having a stop extending inwardly toward the other of the fork members, said stop element limiting a position of said flexible member to said convex position.

10. A flosser apparatus comprising:

a body having a first fork member and a second fork member at an end thereof, said first and second fork members having a space therebetween, said body having a first surface extending into said space and toward said first and second fork members;

a flexible member interposed between said first and second fork members in said space, said flexible member having a second surface extending toward said first surface of said body; and a length of floss having one end affixed to said first fork member and an opposite end affixed to said second fork member, said length of floss being tensioned when said first surface engages said second surface.

11. The flosser apparatus of claim 10, said length of floss extending in a direction, said flexible member being cooperative with said first and second fork members such that said first and second fork members move away from each other upon an application of a force onto said flexible member in a direction transverse to said direction of said length of floss.

12. The apparatus of claim 11, said first surface having a plurality of toothed elements extending upwardly therefrom, said second surface having a plurality of toothed elements extending downwardly therefrom.

13. The apparatus of claim 12, said first and second surfaces extending in direction transverse to said direction of said length of floss.

14. The apparatus of claim 10, flexible member comprising an arcuate member having one end affixed to said first fork member and an opposite end affixed to said second fork member.

15. The apparatus of claim 10, each of said first and second fork members having a bent shape such that said length of floss is offset from a plane of said body.

16. The apparatus of claim 10, one of said first and second surfaces having a button element extending therefrom, the other of said first and second surfaces having an orifice formed thereon, said button element engageable with said orifice.

17. A flosser apparatus comprising:

a body having a first fork member and a second fork member at an end thereof, said first and second fork members having a space therebetween;

an arcuate flexible member interposed between said first and second fork members in said space; and a length of floss having one end affixed to said first fork member and an opposite end affixed to said second fork member, said arcuate flexible member being deformable so as to cause said length of floss to tighten, said body having a first surface extending into said space, said arcuate flexible member having a second surface extending toward said first surface, said first surface being engageable with said second surface so as to fix a distance between said first and second fork members and to retain said length of floss in a tightened position.

* * * * *